United States Patent [19]
Lacey, Jr.

[11] Patent Number: 5,606,110
[45] Date of Patent: Feb. 25, 1997

[54] DIAPHRAGM CONSTRUCTION FOR FREE PISTON SHOCK TUBE/TUNNEL

[75] Inventor: John J. Lacey, Jr., Minnetonka, Minn.

[73] Assignee: Aero Systems, Engineering, Inc., St. Paul, Minn.

[21] Appl. No.: 304,917

[22] Filed: Sep. 13, 1994

[51] Int. Cl.⁶ .................................................. G01N 3/30
[52] U.S. Cl. ............................................. 73/12.08; 73/147
[58] Field of Search ............................ 73/11.04, 11.07, 73/12.08, 12.07, 147

[56] References Cited

U.S. PATENT DOCUMENTS

| | | | |
|---|---|---|---|
| 2,537,096 | 1/1951 | Shreeve et al. | 73/12.07 |
| 2,824,444 | 2/1958 | Hanes | 73/12.07 |
| 2,836,063 | 5/1958 | Yoler et al. | 73/12.08 |
| 3,062,036 | 11/1962 | York | 73/12.07 |
| 3,079,786 | 3/1963 | Fowler et al. | 73/12.07 |
| 3,130,575 | 4/1964 | Rogers | 73/12.07 |
| 3,326,033 | 6/1967 | Stephenson et al. | 73/12.08 |
| 3,398,571 | 8/1968 | Montgomery et al. | 73/12.08 |
| 3,398,572 | 8/1968 | Johnson et al. | 73/12.08 |
| 3,431,777 | 3/1969 | Norfleet | 73/12.08 |
| 3,495,455 | 2/1970 | Allgood | 73/12.08 |
| 3,536,054 | 10/1970 | Stephens | 73/12.07 |
| 3,823,600 | 7/1974 | Wolff | 73/12.07 |
| 3,872,709 | 3/1975 | Pagano | 73/12.08 |
| 4,696,182 | 9/1987 | Meir | 73/12.07 |
| 4,898,028 | 2/1990 | Brehm | 73/147 |
| 5,115,665 | 5/1992 | Lacey, Jr. | 73/12.08 |
| 5,245,868 | 9/1993 | Lacey, Jr. | 73/12.07 |

FOREIGN PATENT DOCUMENTS

| | | | |
|---|---|---|---|
| 917024A | 3/1982 | U.S.S.R. | 73/12.08 |
| 8902071 | 3/1989 | WIPO . | |

OTHER PUBLICATIONS

Mar'yasin et al., "Diaphragm–Bursting System for the Chemical Shock Tube", Journal of Engineering Physics, vol. 12, #3, Mar. 1967.

Belykh et al., "Shock Tube for investigation of high–temperature MHD Generators," High Temperature, vol. 14, No. 2, pp. 317–321, Sep. 1976.

Andersen et al., "Shock tube for simulating nuclear blast durations", Rev. Sci. Instrum., 49(12), Dec. 1978.

Primary Examiner—Richard Chilcot
Assistant Examiner—George M. Dombroske
Attorney, Agent, or Firm—Dorsey & Whitney P.L.L.P.

[57] ABSTRACT

A free piston shock tube/tunnel and a diaphragm construction for a free piston shock tube tunnel in which the diaphragm is provided with multiple rupture areas.

11 Claims, 3 Drawing Sheets

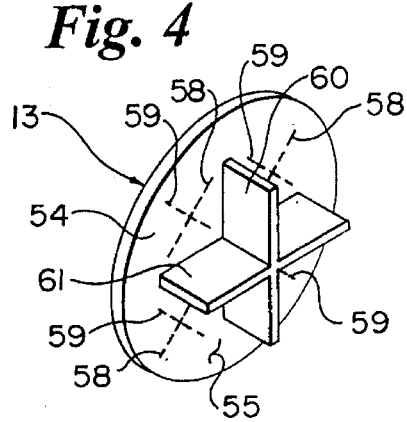
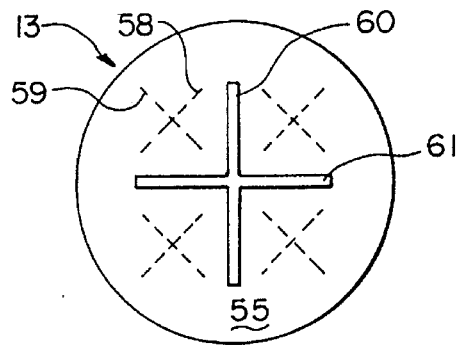
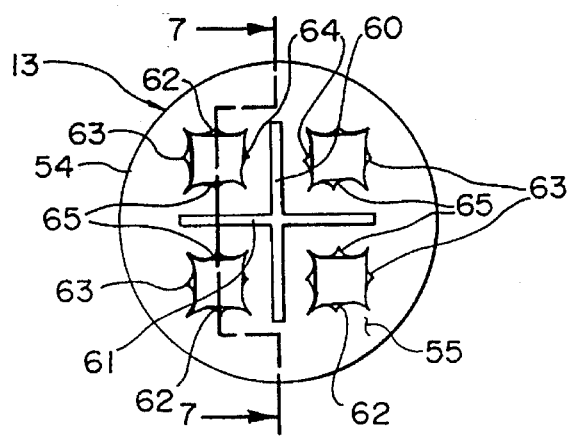
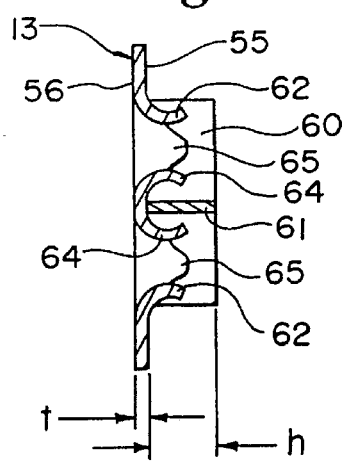

DIAPHRAGM CONSTRUCTION FOR FREE PISTON SHOCK TUBE/TUNNEL

BACKGROUND OF THE INVENTION

1. Field of the Invention

The present invention relates to the field of free piston shock tubes/tunnels, and more particularly, to a diaphragm construction for a free piston shock tube/tunnel.

2. Description of the Prior Art

Free piston shock tube/tunnels have existed since the 1950's. During operation, such shock tube/tunnels are able to generate a shock wave of extremely high pressure and high temperature at a test site for a desired duration or test time. Free piston shock tube/tunnels are principally used to provide aerodynamic test conditions for rocket nose cones, space re-entry vehicles, hypersonic aircraft and the like.

In general, free piston shock tube/tunnels include an elongated, generally cylindrical compression tube containing a compression or driver gas such as helium. The compression tube is normally closed at one end by a diaphragm having a preselected rupture pressure. A compression piston is contained within the compression tube and is adapted for movement from a piston end of the tube toward the diaphragm end. Connected to the diaphragm end of the compression tube is an elongated shock tube having a test end remote from the diaphragm and being filled with a low pressure driven gas such as ambient air. When the piston is moved from the piston starting end of the compression tube toward the diaphragm end, the gas within the compression tube is compressed, thus generating pressure and causing the diaphragm to rupture. The rupturing of the diaphragm causes a volume of the compression gas to pass through the ruptured diaphragm and into the connected shock tube to form a shock wave. The shock wave compresses the driven gas during movement through the shock tube, thereby creating the desired test conditions at the test site. In the case of the shock tunnel, the compressed gas is further processed through a nozzle at the final test site.

An area of free piston shock tubes/tunnels which has received considerable attention has been the area at the diaphragm end of the compression tube. Various improvements and developments have been made relative to this area of the shock tube/tunnel such as the provision of a replaceable orifice insert as disclosed in U.S. Pat. No. 5,115,665 and the provision of a piston stop member as disclosed in U.S. Pat. No. 5,245,868. However, diaphragm construction per se has remained relatively unchanged, with few variations or improvements throughout the years.

Although existing diaphragm design has been reasonably acceptable, high cost continues to be a problem, since the diaphragm must be replaced after each test, as well as the speed with which conventional diaphragms open. Conventional diaphragms have a single, centrally located rupture area designed to rupture along predetermined score lines when exposed to a predetermined pressure in the compression tube. Due primarily to the size of the diaphragm opening which is necessary to achieve certain shock formation and flow characteristics, it has been necessary to construct the diaphragm from relatively thick material such as steel or other metals. Further, the larger the opening, the longer it take for the opening to become fully opened when a rupture of the diaphragm occurs.

Accordingly, there is a need in the art for an improved diaphragm designed for a free piston shock tube/tunnel which is cheaper and which opens at least as quick, and preferably quicker, than conventional single opening diaphragms when exposed to the rupture pressure.

SUMMARY OF THE INVENTION

In contrast to the prior art, the present invention provides an improved diaphragm construction for a free piston shock tube/tunnel which is less expensive than conventional diaphragm construction and which opens quicker than conventional diaphragms when exposed to the preselected rupture pressure. More specifically, the diaphragm design of the present invention is a diaphragm construction having multiple rupture areas rather than a single rupture area as shown in the prior art. The provision of multiple rupture areas facilitates construction of the diaphragm from thinner material than that of the prior art, thereby significantly reducing diaphragm cost. Further, a diaphragm with multiple rupture areas will open quicker than a diaphragm with a single opening.

Preferably, the multiple rupture area diaphragm constructed in accordance with the present invention is also provided with a reinforcement support structure on the shock tube side of the diaphragm so that each of the rupture areas ruptures independently of the other when exposed to the preselected rupture pressure.

Accordingly, it is an object of the present invention to provide an improved diaphragm structure for a free piston shock tube/tunnel which is less expensive than existing diaphragms while maintaining acceptable performance.

Another object of the present invention is to provide a diaphragm construction for a free piston shock tube/tunnel which is provided with two or more rupture areas.

A still further object of the present invention is to provide a diaphragm construction for a free piston shock tube/tunnel having multiple rupture areas and further having a reinforcement structure on the shock tube side of the diaphragm for supporting the diaphragm when exposed to the rupture pressure.

These and other objects of the present invention will become apparent with reference to the drawings, the description of the preferred embodiment and the appended claims.

DESCRIPTION OF THE DRAWINGS

FIG. 4 is an isometric view of a multi-orifice diaphragm, with supporting struts, in accordance with the present invention as viewed from the downstream or shock tube side of the diaphragm.

FIG. 5 is an elevational view from the downstream side of a non ruptured multi-orifice diaphragm, with supporting struts, in accordance with the present invention.

FIG. 6 is an elevational view from the downstream side of a ruptured multi-orifice diaphragm, with supporting struts, in accordance with the present invention.

FIG. 7 is a sectional view as viewed along the section line 7—7 of FIG. 6.

DESCRIPTION OF THE PREFERRED EMBODIMENT

Conventional free piston shock tubes include a compression tube, a shock tube, a piston moveable in the compression tube and a rupturable diaphragm positioned between the compression and shock tubes. A free piston shock tunnel comprises a shock tube in combination with a nozzle and test section. The present invention is applicable to both a free piston shock tube and a free piston shock tube. Accordingly, the term "free piston shock tube/tunnel" as used herein shall mean a free piston shock tube or a free piston shock tunnel.

Figure 1:
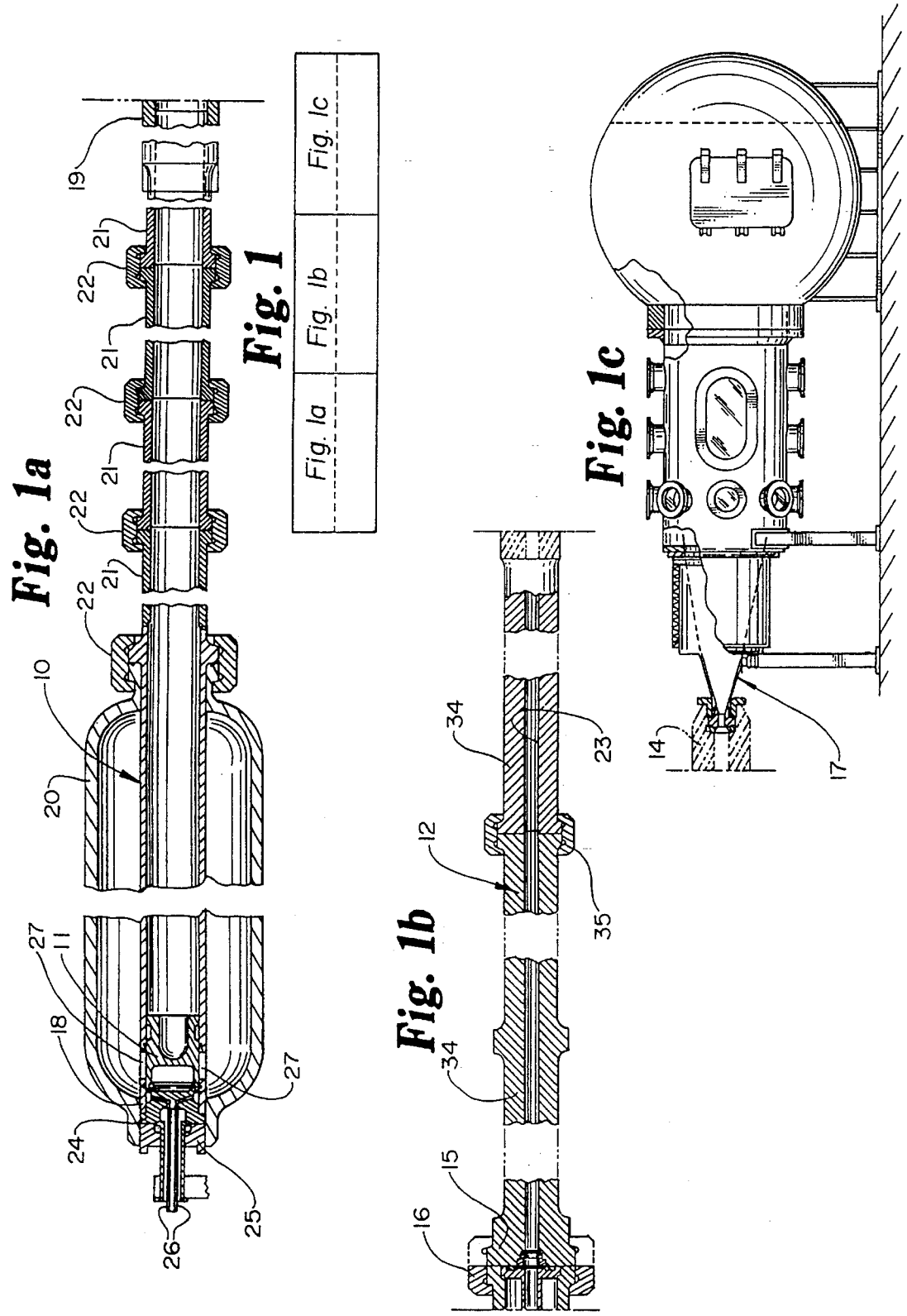
FIG. 1 is comprised of FIGS. 1a, 1b and 1c is a side view, partially in section, of a free piston shock tube/tunnel in accordance with the present invention.

General reference is first made to FIG. 1 showing a side view of the elongated free piston shock tube/tunnel of the present invention. As illustrated, the shock tube/tunnel generally includes an elongated compression tube 10 and an elongated shock tube 12 connected end to end with the compression tube 10 via an appropriate connecting collar 16. A free piston 11 is adapted for movement from one end of the compression tube 10 toward the other for the purpose of compressing a compression gas within the tube 10. A diaphragm 13 (FIGS. 2 and 3) is positioned in the area of connection between the compression tube 10 and the shock tube 12.

In the preferred embodiment, the compression tube 10 has a generally cylindrical configuration and extends from a first or piston end 18 to a second or diaphragm end 19. Normally, the compression tube 10 is constructed of high strength steel and is sufficient to withstand pressures as high as 2,000 atmospheres or more and temperature as high as 7,000K or more. A portion of the compression tube 10 near the piston end 18 is surrounded by a secondary buffer 20 for the purpose of storing the high pressure gas which ultimately accelerates the piston. The actual length of the compression tube 10 is a matter of shock tube/tunnel design. Generally, it is contemplated that the compression tube in a free piston shock tube/tunnel in accordance with the present invention will be at least 33 meters in length. In the preferred embodiment it is shown that the compression tube 10 is made up of a plurality of compression tube sections 21. These are connected with one another by corresponding split hub clamps 22 in a manner known in the art. The compression tube 10 is filled with a driver gas such as helium which is capable of undergoing a generally quasi-steady adiabatic compression during movement of the piston. Various other gases, however, may also be used.

The piston end 18 of the compression tube 10 is closed by a closure head 24 which is retained relative to the compression tube 10 and the buffer 20 via the end nut 25. The end nut 25 is threadedly retained by internal threads at the end of the buffer 20. Conventional means 26 as provided for the purpose of introducing a compression piston driving gas behind the piston 11 for the purpose of driving the piston toward the right as viewed in FIG. 1. As the piston 11 moves forwardly toward the right as viewed in FIG. 1, the ports 27 in the compression tube 10 are opened. This allows the gas from the buffer 20 to flow into the volume behind the piston 11, thereby causing its acceleration. The buffer gas can be compressed to a pressure of 200 arm or greater. It is contemplated that the mechanism for controlling the actuation and driving of the piston 11 will be similar to those known in the art.

The shock tube 12 includes a first or diaphragm end 15 and a second or test end 14. As illustrated in FIG. 1 and also in FIGS. 2 and 3, the diaphragm end 15 of the shock tube 12 is connected with the diaphragm end 19 of the compression tube 10 via the hub clamp 16. The test end 14 of the shock tube 12 is provided with any appropriate test mechanism desired. The preferred embodiment of FIG. 1 illustrates a conventional test end for a shock tunnel, with a conventional test nozzle structure 17 associated with the shock tube 12 for testing purposes. It is contemplated, however, that the nozzle structure 17 could be removed, with the structure of the present invention operating as a free piston shock tube.

The shock tube 12 of the preferred embodiment has a generally cylindrical or tubular configuration with an exterior cylindrical surface and an internal cylindrical bore 23. The shock tube 12 is preferably constructed of a material such as high strength steel.

The actual length of the shock tube 12 is a matter of design based upon the test conditions desired and various other parameters. In the preferred embodiment, the test tube 12 is comprised of a plurality of shock tube sections 34 which are connected in end-to-end relationship with on another via the split hub clamps 35.

Figure 2:
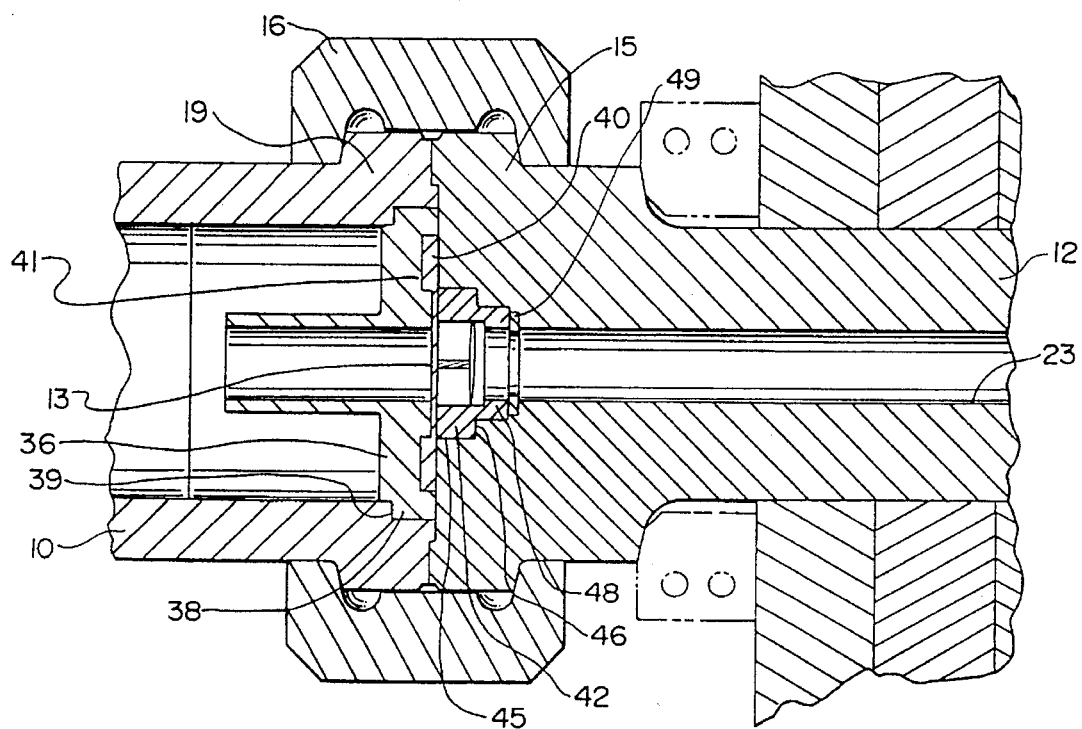
FIG. 2 is an enlarged view, partially in section, of the portion of the free piston shock tube/tunnel in the area of connection between the compression tube and shock tube showing a diaphragm in position for a test run.
Figure 3:
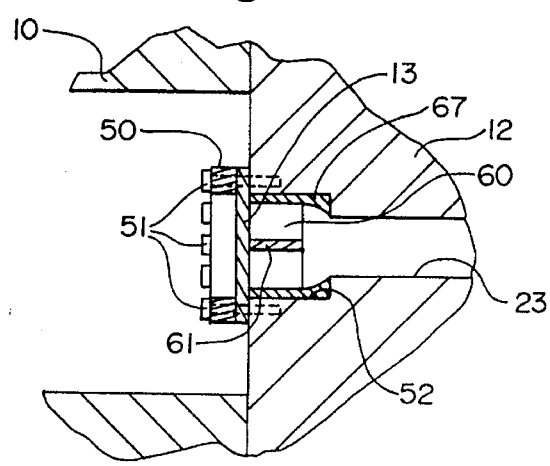
FIG. 3 is a view, partially in section and similar to that of FIG. 2 showing an alternate method of mounting the diaphragm in position for a test run.

As illustrated best in FIGS. 2 and 3, a diaphragm 13 is positioned and retained in the area of connection between the diaphragm ends 19 and 15 of the compression tube 10 and shock tube 12, respectively. The diaphragm 13 which has a predetermined rupture pressure is retained in the embodiment of FIG. 2 by a diaphragm retaining plate 36 disposed at the diaphragm end 19 of the compression tube 10. The diaphragm retaining plate 36 is provided with an outer annular shoulder portion 38 which fits within and is retained by a corresponding annular recessed area 39 in the end 19. The diaphragm 13 has an enlarged annular portion 40 seated within an annular recess 41 in the diaphragm retaining plate 36.

The diaphragm end 15 of the shock tube 12 of FIG. 2 is provided with a replaceable diaphragm impact ring 42 which is seated within a corresponding recess in the end 15. The impact ring 42 includes an outer annular shoulder portion 45 which is adapted for seating engagement within a corresponding recess 46 in the end 15. The outermost end 48 of the impact ring 42 also seats within a corresponding recessed portion of the end 15. The end portion 48 is provided with an internal diameter approximating the internal diameter of the shock tube bore 23. Positioned between the forward end surface of the end 48 and a recessed surface of the shock tube 12 is a selectively replaceable orifice insert 49 having a pair of flat, generally parallel surfaces which are captured and retained between the outermost end of the impact ring 42 and a portion of the shock tube 12.

FIG. 3 is a view similar to that of FIG. 2 and discloses an alternate diaphragm mount. In FIG. 3, the diaphragm 13 is retained by a generally annular diaphragm retaining ring 50 engaging the peripheral edge of the diaphragm. The retaining ring 50 is provided with a plurality of threaded members 51 extending around its periphery and into the diaphragm end of the shock tube 12. In the embodiment of FIG. 3, the orifice insert 42 (FIG. 2) is replaced by the enlarged annular section 52 positioned at the diaphragm end of the shock tube 12 and in communication with the shock tube bore 23.

General reference is next made to FIGS. 2 and 3 and more specific reference to FIGS. 4–7 showing the specific diaphragm construction in accordance with the present invention. FIGS. 4 and 5 show the diaphragm in its unruptured condition, while FIGS. 6 and 7 show the diaphragm in its ruptured condition. The diaphragm 13 comprises a generally disk shaped diaphragm base 54 having a compression tube side 56 and a shock tube side 55. Preferably, the diaphragm 13 is constructed of steel or other metal from which shock tube/tunnel diaphragms are conventionally constructed. The diaphragm of the present invention, as shown best in FIGS. 4 and 5, includes multiple rupture areas defined by the score or rupture lines 58, 59. These rupture lines 58 and 59 define the areas of the diaphragm which will burst or rupture when the preselected rupture pressure in the compression tube is reached. Although the preferred embodiment illustrated in FIGS. 4–7 shows a diaphragm construction with four rupture areas, the benefits of the present invention can also be achieved with multiple rupture areas of less or more than four. With multiple (two or more) rupture areas provided in the diaphragm construction of the present invention, the thickness "t" (FIG. 7) of the diaphragm can be reduced relative to a diaphragm construction with a single rupture area.

The diaphragm 13 of the present invention is provided with a diaphragm support comprising a plurality of supporting struts or members 60, 61 positioned within the diaphragm end of the shock tube 12. The ends of the members 60, 61 are supported within the shock tube 12 such that the diaphragm side of the members 60, 61 engages the downstream side of the diaphragm 13 is supporting relationship when the diaphragm is installed. In the embodiment of FIG. 3, the members 60, 61 are supported by the strut insert 67 positioned within the portion 52. As shown best in FIGS. 4, 5 and 6, the supporting members 60 and 61 extend between adjacent rupture areas to assist in supporting the diaphragm when it is exposed to the predetermined rupture pressure and to facilitate independent opening of each of the rupture areas. Preferably, the height "h" of the supporting members 60 and 61 should be sufficiently large to accommodate the ruptured triangular pedals 62, 63, 64 and 65 as shown in FIGS. 6 and 7.

Although the diaphragm illustrated in FIGS. 4–7 has a generally circular configuration, it can also be provided with other configurations such as a square or rectangular configuration.

Although the description of the preferred embodiment has been quite specific, it is contemplated that various modifications could be made without deviating from the spirit of the present invention. Accordingly, it is contemplated that the scope of the present invention be dictated by the appended claims rather than by the description of the preferred embodiment.

I claim:

1. A free piston shock tube comprising:
   an elongated compression tube having a piston end and a diaphragm end;
   an elongated shock tube having a diaphragm end and a test end, said diaphragm end of said shock tube being connected with said diaphragm end of said compression tube;
   a piston within said compression tube adapted for compression movement from said piston end to said diaphragm end of said compression tube; and
   a diaphragm positioned in the area of connection between said compression tube and said elongated shock tube, said diaphragm having two or more rupture areas.

2. A shock tube of claim 1 wherein each of said rupture areas is defined by one or more score lines.

3. The shock tube of claim 1 wherein said diaphragm is provided with four rupture areas.

4. The shock tube of claim 1 wherein said diaphragm includes a shock tube side and a compression tube side and said shock tube is provided with one or more support members for supporting the shock tube side of said diaphragm.

5. The shock tube of claim 4 wherein said support members includes a pair of support members intersecting one another and extending at right angles relative to one another to define four rupture area accommodating regions.

6. The shock tube of claim 5 wherein said diaphragm is provided with four rupture areas.

7. The shock tube of claim 6 wherein one of said four rupture areas is provided in each of said rupture area accommodating regions.

8. The shock tube of claim 4 wherein each of said rupture areas is provided with one or more score lines defining a plurality of rupture petals.

9. The shock tube of claim 8 wherein said support members are provided with a height sufficient to accommodate said rupture petals.

10. The shock tube of claim 1 wherein each of said rupture areas is provided with one or more score lines defining a plurality of rupture petals.

11. A free piston shock tunnel comprising the free piston shock tube of claim 1.

* * * * *